(12) United States Patent
Kuwabara et al.

(10) Patent No.: US 7,723,522 B2
(45) Date of Patent: May 25, 2010

(54) PYRIDINE DERIVATIVE PRODUCTION METHOD

(75) Inventors: Hirokazu Kuwabara, Kanagawa (JP);
Chang Shan Zhang, Kanagawa (JP);
Hiromitsu Saitoh, Kanagawa (JP);
Takayuki Sonoda, Kanagawa (JP)

(73) Assignee: Fujifilm Finechemicals Co., Ltd, Tokyo (JP)

( * ) Notice: Subject to any disclaimer, the term of this patent is extended or adjusted under 35 U.S.C. 154(b) by 1340 days.

(21) Appl. No.: 11/046,743

(22) Filed: Feb. 1, 2005

(65) Prior Publication Data
US 2005/0171355 A1  Aug. 4, 2005

(30) Foreign Application Priority Data
Feb. 2, 2004  (JP) .................. P.2004-025806

(51) Int. Cl.
*C07D 221/02*  (2006.01)
*C07D 211/72*  (2006.01)
*C07D 401/00*  (2006.01)
*C07D 213/08*  (2006.01)

(52) U.S. Cl. .................. 546/112; 546/268.1; 546/250; 546/290

(58) Field of Classification Search .................. 546/255, 546/329, 268.1, 250, 290, 112
See application file for complete search history.

(56) References Cited

FOREIGN PATENT DOCUMENTS

| EP | 1 186 597 A1 | 3/2002 |
| EP | 1 186 597 B1 | 6/2004 |
| JP | 2001-261653 A | 9/2001 |
| WO | 99/55830 A2 | 11/1999 |
| WO | WO 99/55830 A2 | 11/1999 |
| WO | WO0146135 * | 6/2001 |

OTHER PUBLICATIONS

Hcaplus 128: 88888 Casreact.*
Hcaplus 128:88888 Casreact Abstract, Nishiwaki et. al., "Nitropyrimidinones. Synthetic equivalents of diformylamine and nitromalonaldehyde", 1997.*
XP-002326848—Abstract (1997) Nagatoshi Nishiwaki et al., vol. 11, pp. 1277-1280.
XP-002326847—Abstract (1988) Akira Katoh et al., vol. 32, No. 8, pp. 2942-2946.
European Search Report dated May 23, 2005.
Ian W. Davies et al., "An Efficient Preparation of Vinamidinium Hexafluorophosphate Salts" (2000) J. Org. Chem., vol. 65, pp. 4571-4574.
Ian W. Davies et al., "A Practical Synthesis of a COX-2-Specific Inhibitor" (2000) J. Org. Chem., vol. 65, pp. 8415-8420.
Jean-Francois Marcoux et al., "A General Preparation of Pyridines and Pyridones via the Annulation of Ketones and Esters" (2001) J. Org. Chem., vol. 66, pp. 4194-4199.
S. Stadler et al., "Determination of the First Hyperpolarizabilities of Octupolar Molecular Ions Made from Symmetric Cyanine Dyes" (1996) Chem. Mater., vol. 8, pp. 676-678.
Z. Arnold "Synthetic Reactions of Dimethylformamide XXI.* Formlyation of Some Carboxylic Acids and Their Derivatives" (1961) Org. Chem., vol. 85, pp. 3051-3058.
Z. Arnold "Not on the Formylation of Chloro-and Bromoacetic Acid" (1964) Org. Chem., vol. 30, pp. 2125-2127.
Douglas Lloyd et al., "Studies of 2-Oxo- and 2-Thioxo-1,2-dihydropyrimidinium Salts" J.C.S. Perkin, pp. 1862-1869.
D. Lloyd et al., "Experiments towards the Preparation of 6-Hydroxy-, 6-Methoxy-, and 6-(Hydroxyphenyl)-2-3-dihydro-1,4-diazepinium Salts and 1,2-Dihydro-5-(hydroxyphenyl)-2-oxopyrimidinium Salts" (1986) Liebigs Ann. Chem . . . , pp. 1368-1379.

* cited by examiner

*Primary Examiner*—Janet L Andres
*Assistant Examiner*—Binta M Robinson
(74) *Attorney, Agent, or Firm*—Sughrue Mion, PLLC

(57) ABSTRACT

A method in which a pyridinium derivative such as 1,3-dimethyl-2,3-dihydro-2-oxopyrimidinium chloride is reacted with an acetyl compound such as 4-acetylpyridine, and then the reaction product is reacted with ammonia or an ammonium salt.

8 Claims, No Drawings

PYRIDINE DERIVATIVE PRODUCTION METHOD

BACKGROUND OF THE INVENTION

1. Field of the Invention

This invention relates to a method for producing a pyridine derivative which is an important intermediate in the field of medicines, agricultural chemicals, catalytic ligands, combinatorial chemistry, organic electroluminescence elements, charge transport materials, electron transport materials, electrophotographic photo-sensitive materials, dyes, liquid crystals and the like.

2. Description of the Related Art

Methods for producing pyridine ring using an acetyl compound as the material have been developed in recent years. For example, a method has been disclosed in which pyridine ring is constructed under a relatively mild condition with a high yield using a vinamidinium compound obtained by carrying out Vilsmeier reaction of a carboxylic acid derivative (cf. International Publication No. 99/55830 and JP-A-2001-261653, "J. Org. Chem., 4571-4574 (2000)", "J. Org. Chem., 8415-8420 (2000)" and "J. Org. Chem., 4194-4199 (2001)". However, this method has two technical problems. One of them is that since dimethylamine, which is volatile and exerts a serious influence upon environment is generated in a large amount, a special gas collector is required for preventing release of this into the air. Also, the other problem is the high cost, because it is difficult to isolate such a vinamidinium compound as a chloride salt, thus resulting in a low yield as a rule (cf. "Chem. Mater., 676 (1996)", "Collect. Czech. Chem. Commun., 3051 (1961)" and "Collect. Czech. Chem. Commun., 2125 (1965)". As a method for solving this problem, a method in which a vinamidinium compound of hexafluorophosphoric acid ($PF_6$) salt is isolated has been disclosed. However, since hexafluorophosphoric acid ($PF_6$) ion severely corrodes glass, a general purpose rector made of glass cannot be used, there is a problem in that a special cost is required for the treatment of waste water containing fluorine ion.

As a method, which does not use an ionic precursor, a method is also known in which pyridine ring is constructed by an aminoacrolein derivative (cf. abovementioned "J. Org. Chem., 4571-4574 (2000)", "J. Org. Chem., 8415-8420 (2000)" and "J. Org. Chem., 4194-4199 (2001)"). However, this method also has a problem in that dimethylamine is generated by the reaction.

On the other hand, as a method for synthesizing a pyrimidinium salt, a method is known in which it is synthesized from a malonaldehyde compound or a vinamidinium compound and a urea derivative (cf. "J. Chem. Soc. Perkin Trans. 1, 1862-1869 (1977)" and "Liebigs Ann. Chem., 1368-1379 (1986)". However, synthesis from a vinamidinium compound cannot avoid the problem of causing corrosion and bad smell, but rather results in the increase of cost because the number of processes is increased, so that a more inexpensive production method has been in demand.

SUMMARY OF THE INVENTION

The object of the invention is to provide a method for producing a pyridine derivative, an important intermediate in the field of medicines, agricultural chemicals, catalytic ligands, combinatorial chemistry, organic electroluminescence elements, charge transport materials, electron transport materials, electrophotographic photo-sensitive materials, dyes, liquid crystals and the like, without using an expensive catalyst and a special facilities, which method can be conducted on an industrial scale. More illustratively, it is to provide a method for producing a regiospecific pyridine derivative, which can be produced at a high purity, a high yield and a low cost without causing a pollution problem.

With the aim of attaining the aforementioned object, the present inventors have conducted intensive studies and succeeded as a result in developing a pyridine derivative production method, which can solve the aforementioned problems, thus resulting in the accomplishment of the invention. That is, the invention is achieved by the following methods.

(1) A method for producing a pyridine derivative represented by formula (III) below, the method comprising reacting a pyrimidinium derivative represented by formula (I) below, an acetyl compound represented by formula (II) below and an ammonia or an ammonium salt:

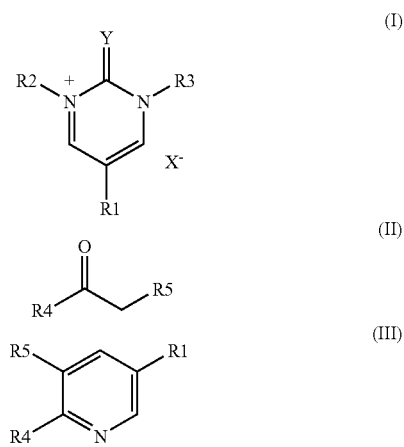

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, nitro group, cyano group, halogen atom or hetero ring residue;

R2 represents alkyl group, alkenyl group, alkynyl group, aryl group, carbonyl group, sulfonyl group, carbamoyl group, sulfamoyl group, amino group, ureido group, carbonylamino group, sulfonylamino group, cyano group or hetero ring residue;

R3 represents alkyl group, alkenyl group, alkynyl group, aryl group, hydroxyl group, alkoxy group, aryloxy group, carbonyloxy group, alkylthio group, arylthio group, carbonyl group, oxycarbonyl group, sulfonyl group, carbamoyl group, sulfamoyl group, amino group, ureido group, carbonylamino group, sulfonylamino group, nitro group, cyano group, hetero ring residue or halogen atom;

R4 represents hydrogen atom, alkyl group, alkenyl group, alkynyl group, aryl group, amino group, formyl group, carboxyl group, carbonyl group, oxycarbonyl group, sulfo group, sulfonyl group, carbamoyl group, sulfamoyl group, cyano group or hetero ring residue;

R5 represents hydrogen atom, alkyl group, alkenyl group, alkynyl group, aryl group, hydroxyl group, alkoxy group, aryloxy group, carbonyloxy group, formyl group, carboxyl group, carbonyl group, oxycarbonyl group, sulfonyl group, alkylthio group, arylthio group, carbamoyl group, sulfamoyl group, nitro group, cyano group, hetero ring residue or halogen atom, wherein R4 and R5 may be bonded to form a ring consisting of at least one non-metallic atom, the ring including the carbon atoms to which R4 and R5 are bonded;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring residue, wherein R6 may be bonded with R2 or R3 to form a hetero ring including the nitrogen atom to which R2 or R3 is bonded; and $X^-$ represents an anion.

(2) A method for producing a pyrimidinium derivative represented by formula (I) below, the method comprising reacting at least one of a bisacetal compound represented by formula (IV) below and an acrolein compound represented by formula (V) below with a urea compound represented by formula (VI) below:

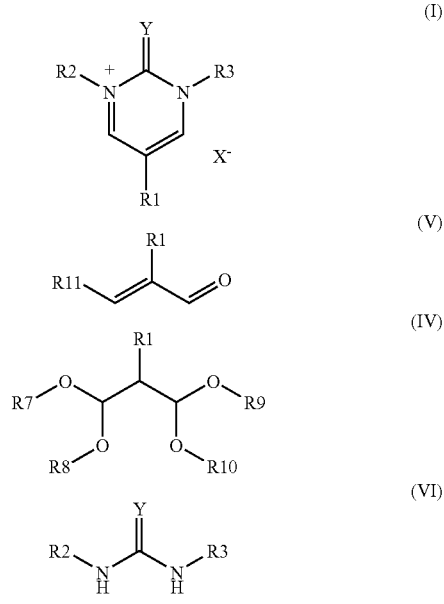

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, nitro group, cyano group, halogen atom or hetero ring residue;

R2 represents alkyl group, alkenyl group, alkynyl group, aryl group, carbonyl group, sulfonyl group, carbamoyl group, sulfamoyl group, amino group, ureido group, carbonylamino group, sulfonylamino group, cyano group or hetero ring residue;

R3 represents alkyl group, alkenyl group, alkynyl group, aryl group, hydroxyl group, alkoxy group, aryloxy group, carbonyloxy group, alkylthio group, arylthio group, carbonyl group, oxycarbonyl group, sulfonyl group, carbamoyl group, sulfamoyl group, amino group, ureido group, carbonylamino group, sulfonylamino group, nitro group, cyano group, hetero ring residue or halogen atom;

$X^-$ represents an anion;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring residue, wherein R6 may be bonded with R2 or R3 to form a hetero ring including the nitrogen atom to which R2 or R3 is bonded;

R7 to R10 each independently represents alkyl group, wherein two of R7 to R10 may be bonded to form a ring consisting of at least one non-metallic atom, the ring including the oxygen atoms to which said two of R7 to R10 are bonded; and R11 represents alkoxy group, aryloxy group, di-substituted amino group or hetero ring residue.

(3) The method for producing the pyridine derivative as described in (1) above, wherein an amount of the pyrimidinium derivative is from 0.5 to 6.0 mol based on 1 mol of the acetyl compound.

(4) The method for producing the pyridine derivative as described in (1) or (3) above, further comprising:

reacting at least one of a bisacetal compound represented by formula (IV) below and an acrolein compound represented by formula (V) below with a urea compound represented by formula (VI) below to produce the pyrimidinium derivative represented by formula (I); and reacting the pyrimidinium derivative with the acetyl compound represented by formula (II) in a one-pot process:

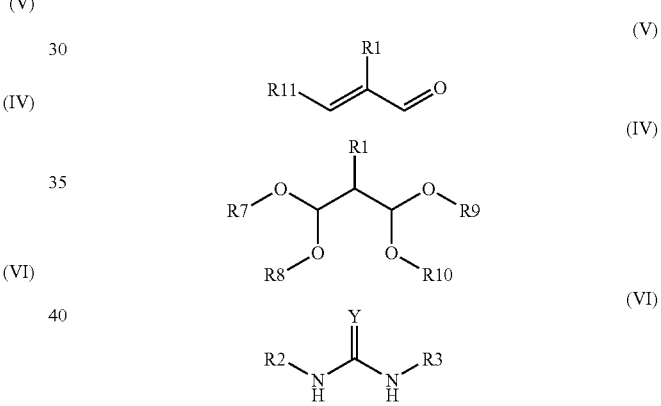

wherein R1 to R3 and Y are the same as defined in (1) above;

R7 to R10 each independently represents alkyl group, wherein two of R7 to R10 may be bonded to form a ring consisting of at least one non-metallic atom, the ring including the oxygen atoms to which said two of R7 to R10 are bonded; and R11 represents alkoxy group, aryloxy group, di-substituted amino group or hetero ring residue.

(5) The method for producing the pyrimidinium derivative as described in (2) above, wherein an amount of the urea compound is from 0.1 to 10 mol based on 1 mol of said at least one of the bisacetal compound and the acrolein compound.

(6) A method for producing a pyridine derivative represented by formula (III) below, the method comprising a simultaneous reaction with at least one of a bisacetal compound represented by (IV) below, an acrolein compound represented by formula (V) below and a malonaldehyde compound formula (VII) below, a urea compound represented by formula (VI) below and an acetyl compound represented by formula (II) below:

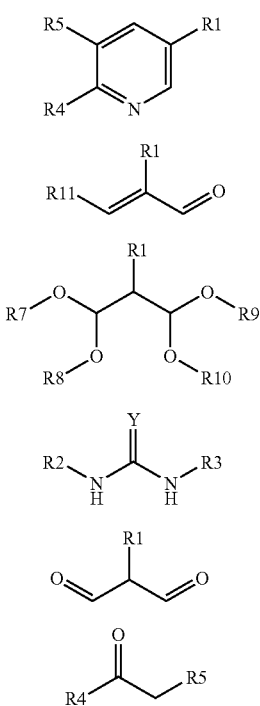

(III)

(V)

(IV)

(VI)

(VII)

(II)

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, nitro group, cyano group, halogen atom or hetero ring residue;

R2 represents alkyl group, alkenyl group, alkynyl group, aryl group, carbonyl group, sulfonyl group, carbamoyl group, sulfamoyl group, amino group, ureido group, carbonylamino group, sulfonylamino group, cyano group or hetero ring residue;

R3 represents alkyl group, alkenyl group, alkynyl group, aryl group, hydroxyl group, alkoxy group, aryloxy group, carbonyloxy group, alkylthio group, arylthio group, carbonyl group, oxycarbonyl group, sulfonyl group, carbamoyl group, sulfamoyl group, amino group, ureido group, carbonylamino group, sulfonylamino group, nitro group, cyano group, hetero ring residue or halogen atom;

R4 represents hydrogen atom, alkyl group, alkenyl group, alkynyl group, aryl group, amino group, formyl group, carboxyl group, carbonyl group, oxycarbonyl group, sulfo group, sulfonyl group, carbamoyl group, sulfamoyl group, cyano group or hetero ring residue;

R5 represents hydrogen atom, alkyl group, alkenyl group, alkynyl group, aryl group, hydroxyl group, alkoxy group, aryloxy group, carbonyloxy group, formyl group, carboxyl group, carbonyl group, oxycarbonyl group, sulfonyl group, alkylthio group, arylthio group, carbamoyl group, sulfamoyl group, nitro group, cyano group, hetero ring residue or halogen atom, wherein R4 and R5 may be bonded to form a ring consisting of at least one non-metallic atom, the ring including the carbon atoms to which R4 and R5 are bonded;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring residue, wherein R6 may be bonded with R2 or R3 to form a hetero ring including the nitrogen atom to which R2 or R3 is bonded;

R7 to R10 each independently represents alkyl group, wherein two of R7 to R10 may be bonded to form a ring consisting of at least one non-metallic atom, the ring including the oxygen atoms to which said two of R7 to R10 are bonded; and R11 represents alkoxy group, aryloxy group, di-substituted amino group or hetero ring residue.

(7) The method for producing the pyridine derivative as described in (6) above, wherein an amount of the urea compound is from 0.001 to 10 mol based on 1 mol of the acetyl compound.

(8) The method for producing the pyridine derivative as described in (6) or (7) above, wherein an amount of said at least one of the bisacetal compound, the acrolein compound and the malonaldehyde compound is from 0.1 to 10 mol based on 1 mol of the acetyl compound.

(9) A method for producing a pyridine derivative represented by formula (III) below, the method comprising reacting at least one of a pyrimidone compound represented by formula (VIII) below and a pyrimidine compound represented by formula (IX) below, an acetyl compound represented by formula (II) below and an ammonia or an ammonium salt:

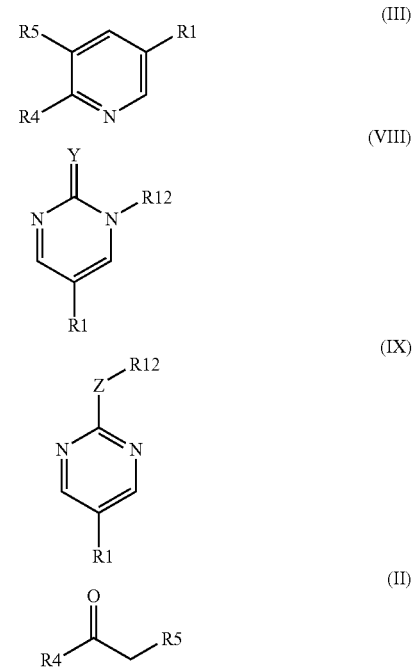

(III)

(VIII)

(IX)

(II)

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, nitro group, cyano group, halogen atom or hetero ring residue;

R4 represents hydrogen atom, alkyl group, alkenyl group, alkynyl group, aryl group, amino group, formyl group, carboxyl group, carbonyl group, oxycarbonyl group, sulfo group, sulfonyl group, carbamoyl group, sulfamoyl group, cyano group or hetero ring residue;

R5 represents hydrogen atom, alkyl group, alkenyl group, alkynyl group, aryl group, hydroxyl group, alkoxy group, aryloxy group, carbonyloxy group, formyl group, carboxyl group, carbonyl group, oxycarbonyl group, sulfonyl group, alkylthio group, arylthio group, carbamoyl group, sulfamoyl group, nitro group, cyano group, hetero ring residue or halogen atom, wherein R4 and R5 may be bonded to form a ring consisting of at least one non-metallic atoms, the ring including the carbon atoms to which R4 and R5 are bonded;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring residue, wherein R6 may be bonded with R2 or R3 to form a hetero ring including the nitrogen atom to which R2 or R3 is bonded;

R12 represents carbonyl group, sulfonyl group, carbamoyl group or sulfamoyl group;

Z represents oxygen atom, sulfur atom, selenium atom or —N(R13); and

R13 represents alkyl group, alkenyl group, alkynyl group or aryl group.

(10) The method for producing the pyridine derivative as described in (9) above, wherein an amount of said at least one of the pyrimidone compound and the pyrimidine compound is from 0.5 to 6.0 mol based on 1 mol of the acetyl compound.

DETAILED DESCRIPTION OF THE INVENTION

The invention is described in the following further in detail.

In order to describe the invention more illustratively, an embodiment of the method of the invention is described as an example in the following, but the contents of the invention are not limited thereto.

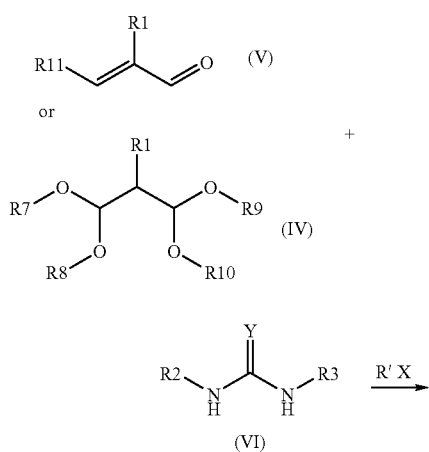

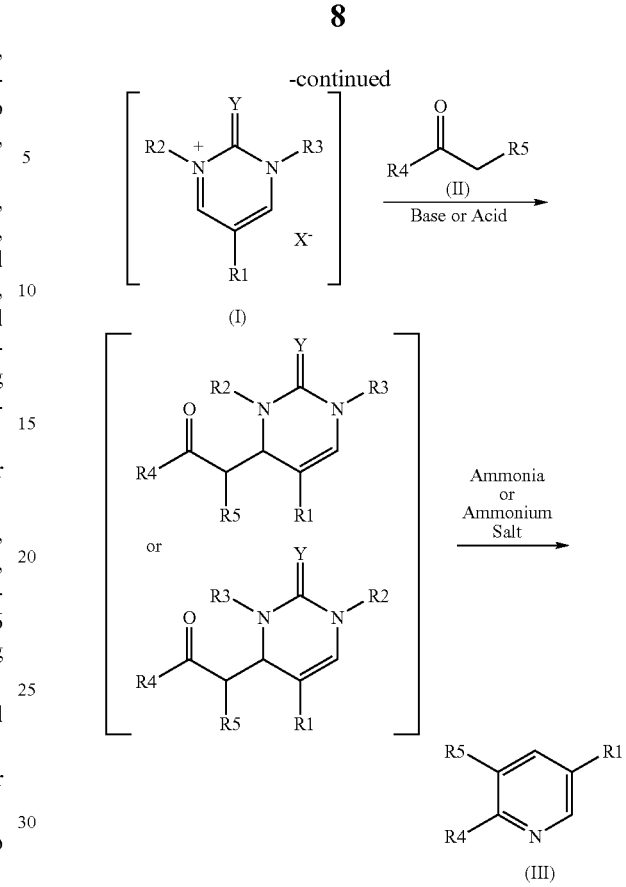

In the above formulae, R1 to R11 and X⁻ are as defined in the foregoing. R' represents hydrogen atom, an onium compound, an alkali metallic atom, an alkaline earth metallic atom, a typical metallic atom, a transition metallic atom or non-metallic atom.

Regarding the general formulae (I) to (IX) of the invention, illustrative examples of the alkyl group represented by R1 to R10 and R13 include methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, cyclopropyl, cyclobutyl, cyclopentyl, cyclohexyl, cycloheptyl, cyclooctyl, cyclononyl, cyclodecyl and the like straight chain, branched or cyclic alkyl groups having from 1 to 20 carbon atoms.

The alkenyl group represented by R1 to R6 and R13 represents vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, hexadienyl, dodecatrienyl and the like straight chain, branched or cyclic alkenyl groups having from 2 to 20 carbon atoms.

The alkynyl group represented by R1 to R6 and R13 represents ethynyl, butynyl, pentynyl, hexynyl, heptinyl, octynyl, nonynyl, cyclooctynyl, cyclononynyl, cyclodecynyl and the like straight chain, branched or cyclic alkynyl groups having from 2 to 20 carbon atoms.

The aryl group represented by R1 to R6 and R13 represents phenyl, naphthyl, phenanthryl, anthryl and the like 6- to 10-membered monocyclic or polycyclic aryl groups.

The alkoxy group represented by R1 to R6 and R11 represents methoxy, ethoxy, propoxy, butoxy, pentyloxy, hexyloxy, heptyloxy, octyloxy, nonyloxy, decyloxy, dodecyloxy, octadecyloxy and the like alkoxy groups having from 1 to 20 carbon atoms.

The aryloxy represented by R1 to R6 represents phenoxy, naphthyloxy and the like.

The carbonyl group represented by R1 to R6 and R12 represents acetyl, propionyl, butyryl, pentanoyl, hexanoyl, valeryl, octanoyl and the like alkyl carbonyl groups; benzoyl, naphthoyl and the like aryl carbonyl groups; methoxycarbonyl, ethoxycarbonyl, tert-butoxycarbonyl, n-decyloxycarbonyl, n-hexadecyloxycarbonyl and the like alkoxy carbonyl groups; and phenoxycarbonyl, naphthyloxycarbonyl and the like aryloxy carbonyl groups.

The sulfonyl group represented by R1 to R6 and R12 represents methylsulfonyl, ethylsulfonyl, propylsulfonyl, butylsulfonyl, pentylsulfonyl, hexylsulfonyl, octylsulfonyl, dodecylsulfonyl, hexadecylsulfonyl and the like alkyl sulfonyl groups; phenylsulfonyl, naphthylsulfonyl and the like aryl sulfonyl groups; methoxysulfonyl, ethoxysulfonyl, tert-butoxysulfonyl, n-decyloxysulfonyl, n-hexadecyloxysulfonyl and the like alkoxy sulfonyl groups; and phenoxysulfonyl, naphthyloxysulfonyl and the like aryloxy sulfonyl groups.

The carbamoyl group represented by R1 to R6 and R12 represents carbamoyl; N-methylcarbamoyl, N-(tert-butyl) carbamoyl, N-dodecylcarbamoyl, N-octadecylcarbamoyl, N-phenylcarbamoyl and the like mono-substituted carbamoyl groups; and N,N-dimethylcarbamoyl, N,N-dihexylcarbamoyl, N,N-didodecylcarbamoyl, N,N-diphenylcarbamoyl and the like di-substituted carbamoyl groups.

The sulfamoyl group represented by R1 to R6 and R12 represents sulfamoyl; N-ethylsulfamoyl, N-(iso-hexyl)sulfamoyl, N-decylsulfamoyl, N-hexadecylsulfamoyl, N-phenylsulfamoyl and the like mono-substitutedsulfamoyl groups; and N,N-dimethylsulfamoyl, N,N-dibutoxysulfamoyl, N,N-dioctylsulfamoyl, N,N-tetradecylsulfamoyl, N,N-diphenylsulfamoyl and the like di-substituted sulfamoyl groups.

The carbonyloxy group represented by R1, R3 and R5 represents acetyloxy, ethylcarbonyloxy, propylcarbonyloxy, hexylcarbonyloxy, dodecylcarbonyloxy, benzoylcarbonyloxy, naphthylcarbonyloxy and the like.

The alkylthio group represented by R1, R3 and R5 represents methylthio, ethylthio, propylthio, butylthio, pentylthio, hexylthio, heptylthio, octylthio, nonylthio, decylthio, dodecylthio, hexadecylthio, octadecylthio and the like alkyltio groups having from 1 to 20 carbon atoms.

The arylthio group represented by R1, R3 and R5 represents phenylthio, naphthylthio and the like.

The amino group represented by R1 to R4 and R6 represents amino; N-methylamino, N-butylamino, N-hexylamino, N-decylamino, N-tetradecylamino, N-octadecylamino, N-phenylamino, N-naphthylamino and the like mono-substituted amino groups; and N,N-diethylamino, N,N-diheptylamino, N,N-dioctylamino, N,N-dodecylamino, N,N-octadecylamino, N,N-diphenylamino and the like di-substituted amino groups.

The di-substituted amino group represented by R11 represents N,N-dimethylamino, N,N-diethylamino, N,N-di(tert-butyl)amino, N,N-dioctylamino, N,N-dodecylamino, N,N-octadecylamino, N,N-diphenylamino, N,N-dinaphthylamino, N-ethyl-N-methylamino, N-ethyl-N-dodecylamino, N-ethyl-N-phenylamino, N-phenyl-N-octylamino and the like.

The carbonylamino group represented by R1 to R3 represents acetylamino, ethylcarbonylamino, tert-butylcarbonylamino, n-octylcarbonylamino, n-hexadecylcarbonylamino, benzoylamino, naphthoylamino, methoxycarbonylamino, ethoxycarbonylamino, n-octyloxycarbonylamino, n-hexadecyloxycarbonylamino and the like.

The sulfonylamino group represented by R1 to R3 represents methylsulfonylamino, ethylsulfonylamino, tert-butylsulfonylamino, n-hexylsulfonylamino, iso-dodecylsulfonylamino, n-octadecylsulfonylamino, phenylsulfonylamino, naphthylsulfonylamino and the like.

The hetero ring residue represented by R1 to R6 and R11 represents a 5- to 10-membered monocyclic or bicyclic heterocyclic group containing from 1 to 4 atoms selected from nitrogen, oxygen and sulfur, such as thiophene, furan, pyran, pyridine, pyrrole, pyrazine, azepine, azocine, azonine, azecine, oxazole, thiazole, pyrimidine, pyridazine, triazine, triazole, tetrazole, imidazole, pyrazole, morpholine, thiomorpholine, piperidine, piperazine, quinoline, isoquinoline, indole, isoindole, quinoxaline, phthalazine, quinolizine, quinazoline, quinoxaline, naphthyridine, chromene, benzofuran, benzothiophene and the like.

The halogen atom represented by R1, R3 and R5 represents chlorine atom, bromine atom, iodine atom, fluorine atom and the like.

The onium compound represented by R' illustratively represents tetrabutylammonium, chlorotris(dimethylamino) phosphonium, triphenylsulfonium and the like.

R4 and R5 may be bonded to form a substituted or unsubstituted ring consisting of a non-metallic atom together with the carbon atoms to which they are bonded, and its illustrative examples include cyclopentanone, cyclohexanone, benzocyclopentanone, benzocyclohexanone, tetrahydropyran-4-one and the like.

R6 may be bonded with R2 or R3 to form a hetero ring together with the nitrogen atoms to which they are bonded, and its illustrative examples include imidazole, 1,3,4-triazole, 1,3,5-triazin-2-one, 1,3-imidazol-4-one, pyrimidin-4-one, 2H-1,2,4-thiadiazine and the like.

Two groups among R7 to R10 may be bonded to form a ring consisting of a non-metallic atom together with the oxygen atoms to which they are bonded, and its illustrative examples include 1,3-dioxolan, 1,3-dioxane, 2,2-dimethyl-1,3-dioxolan, 1,3,5-trioxan and the like.

Illustrative examples of the $X^-$ include fluorine atom, chlorine atom, bromine atom, iodine atom and the like halogen ions; sulfate ion, phosphate ion, nitrate ion, tetrafluoroborate ion, hexafluorophosphate ion, perchlorate ion and the like inorganic acid ion; tetrachloroaluminum ion, tetrabromoferrate (III) ion and the like Lewis acid-containing ions; and acetate ion, lactate ion, citrate ion, benzoate ion, methanesulfonate ion, ethanesulfonate ion, benzenesulfonate ion, toluenesulfonate ion, trifluoroacetate ion, trifluoromethanesulfonate ion, isethionate ion, glucuronate ion, gluconate ion, tetraphenylborate ion and the like organic acid ions. The $X^-$ may be bonded to the general formula (I) to form a betaine structure, and this form is also included in the pyrimidinium derivative of the invention represented by the general formula (I). In that case, the R1 illustratively represents $—SO_3^-$, $—PhSO_3^-$, $—COO^-$, $—CH_2COO^-$, $—OPO_3H^-$ and the like.

These R1 to R13 may be further have substituent groups which are not particularly limited with the proviso that they are not concerned in the reaction. Their illustrative examples include methyl, ethyl, propyl, butyl, pentyl, hexyl, heptyl, octyl, nonyl, decyl and the like alkyl groups; vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, hexadienyl, dodecatrienyl and the like alkenyl groups; ethynyl, butynyl, pentynyl, hexynyl, heptinyl, octynyl, nonynyl, cyclooctynyl, cyclononynyl, cyclodecynyl and the like alkynyl groups; phenyl, naphthyl, phenanthryl, anthryl and the like monocyclic or bi- to tetra-cyclic aryl groups; methoxy, ethoxy, propoxy, butoxy, pentyloxy, hexyloxy, heptyloxy, octyloxy, nonyloxy, decyloxy and the like alkoxy groups; phenoxy, naphthyloxy and the like aryloxy groups; dimethylamino, N-ethyl-N-phenylamino, diphenylamino, N-phenyl-N-naphthylamino and the like disubstituted amino groups; nitro group; furyl, thienyl, pyridyl and the like hetero ring groups; and fluorine atom, chlorine atom, bromine atom, iodine atom and the like halogen atoms. Preferred are alkyl groups, aryl groups, hetero ring residues and halogen atoms, and more preferred alkyl groups and aryl groups.

R1 is preferably hydrogen atom, an alkyl group having from 1 to 12 carbon atoms, an aryl group having from 6 to 20 carbon atoms, a halogen atom or a hetero ring residue, more preferably an alkyl group having from 1 to 6 carbon atoms, an aryl group having from 6 to 12 carbon atoms or a nitrogen-containing hetero ring residue.

R2 is preferably an alkyl group having from 1 to 12 carbon atoms, an aryl group having from 6 to 20 carbon atoms or a hetero ring residue, more preferably an alkyl group having from 1 to 6 carbon atoms or an aryl group having from 6 to 12 carbon atoms.

R3 is preferably an alkyl group having from 1 to 12 carbon atoms, an aryl group having from 6 to 20 carbon atoms or a hetero ring residue, more preferably an alkyl group having from 1 to 6 carbon atoms or an aryl group having from 6 to 12 carbon atoms.

R4 is preferably hydrogen atom, an alkyl group having from 1 to 12 carbon atoms, an aryl group having from 6 to 20 carbon atoms or a hetero ring residue, more preferably an alkyl group having from 1 to 6 carbon atoms, an aryl group having from 6 to 12 carbon atoms or a nitrogen-containing hetero ring residue.

R5 is preferably hydrogen atom, an alkyl group having from 1 to 12 carbon atoms, an aryl group having from 6 to 20 carbon atoms, an alkyl carbonyl group having from 2 to 10 carbon atoms, an alkoxy carbonyl having from 2 to 10 carbon atoms or a nitrogen-containing hetero ring residue, more preferably hydrogen atom, a lower alkyl group having from 1 to 4 carbon atoms, phenyl group or an alkoxy carbonyl group having from 2 to 5 carbon atoms.

R6 is preferably an alkyl group having from 1 to 12 carbon atoms, an aryl group having from 6 to 20 carbon atoms or sulfonyl group, more preferably an alkyl group having from 1 to 6 carbon atoms or an aryl group having from 6 to 12 carbon atoms.

R7 to R10 are preferably an alkyl group having from 1 to 12 carbon atoms, an aryl group having from 6 to 20 carbon atoms or a hetero ring residue, more preferably an alkyl group having from 1 to 6 carbon atoms, an aryl group having from 6 to 12 carbon atoms or an oxygen-containing hetero ring residue.

R11 is preferably an alkoxy group having from 1 to 12 carbon atoms, an alkylamino group having from 1 to 12 carbon atoms or a hetero ring residue, more preferably an alkoxy group having from 1 to 6 carbon atoms, an alkylamino group having from 1 to 6 carbon atoms or a nitrogen-containing hetero ring residue.

R12 is preferably an alkyl carbonyl group having from 2 to 13 carbon atoms, an alkoxy carbonyl group having from 2 to 13 carbon atoms, phenylcarbonyl group, phenoxycarbonyl group or an alkyl sulfonyl group having from 1 to 12 carbon atoms, more preferably an alkyl carbonyl group having from 2 to 5 carbon atoms, an alkoxy carbonyl group having from 2 to 5 carbon atoms, phenylcarbonyl group, or an alkyl sulfonyl group having from 1 to 4 carbon atoms.

R13 is preferably an alkyl group having from 1 to 12 carbon atoms or an aryl group having from 6 to 20 carbon atoms, more preferably an alkyl group having from 1 to 6 carbon atoms or an aryl group having from 6 to 12 carbon atoms.

$X^-$ is preferably chlorine atom, bromine atom, sulfate ion, tetrafluoroborate ion, acetate ion, methanesulfonate ion or $-SO_3^-$ as a betaine structure, more preferably chlorine ion, tetrafluoroborate ion or methanesulfonate ion.

Illustrative examples of the pyridine derivative represented by general formula (III), the pyrimidinium derivative represented by general formula (I), the pyrimidone compound represented by general formula (VIII) and the pyrimidine compound represented by general formula (IX) are shown below, though the invention is not restricted by these compounds.

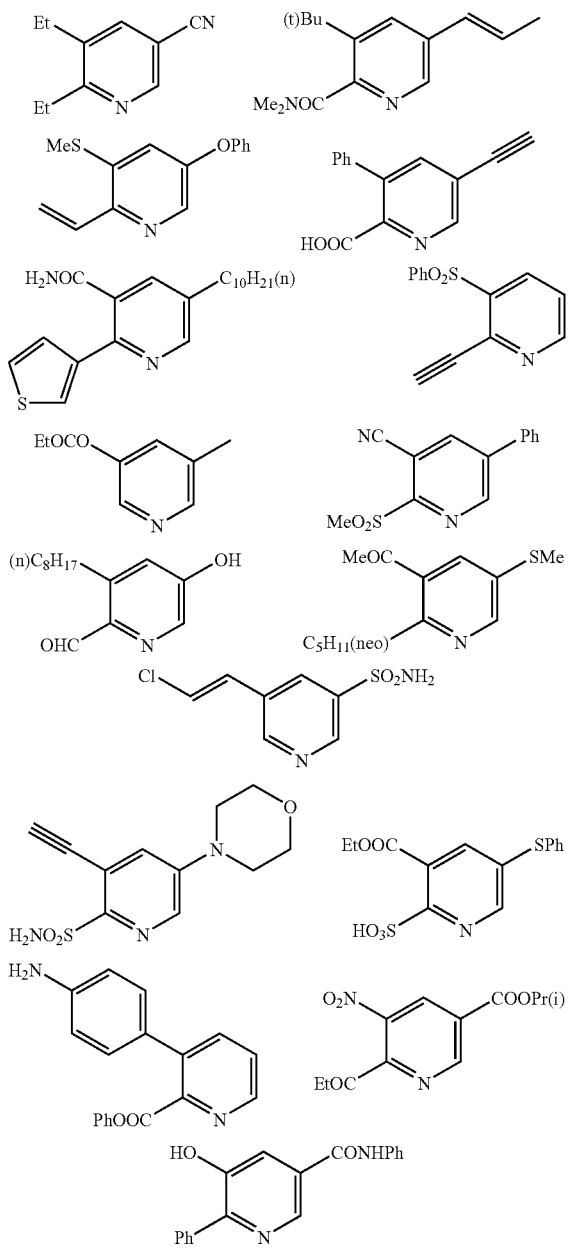

-continued
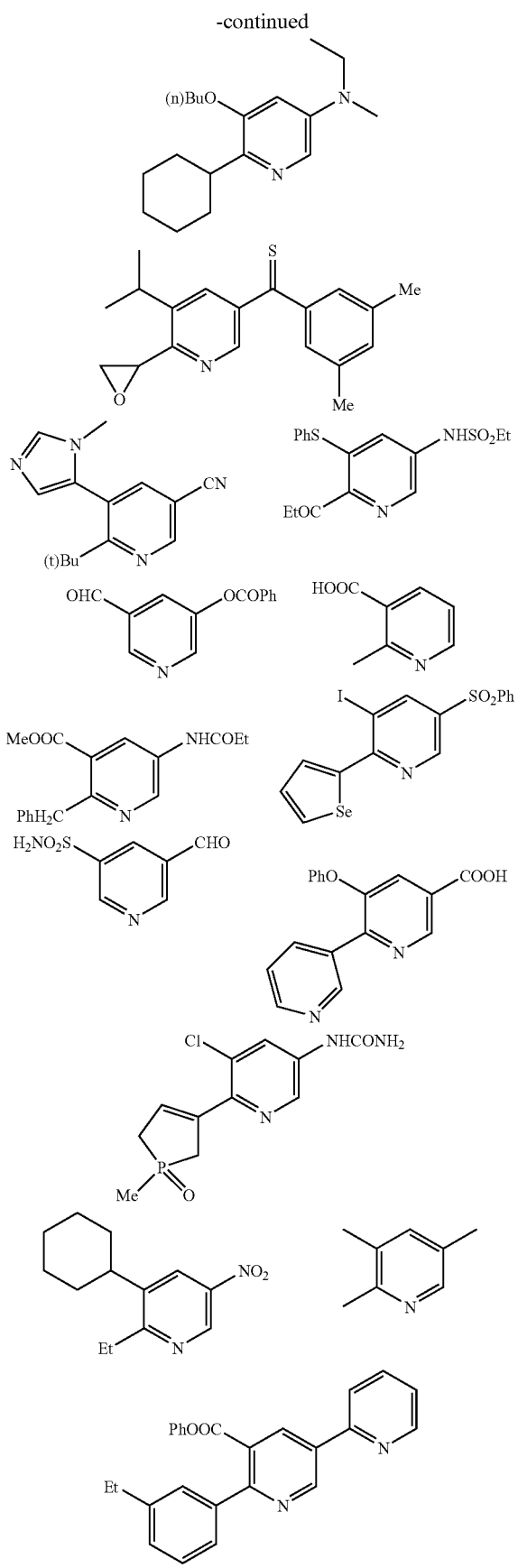
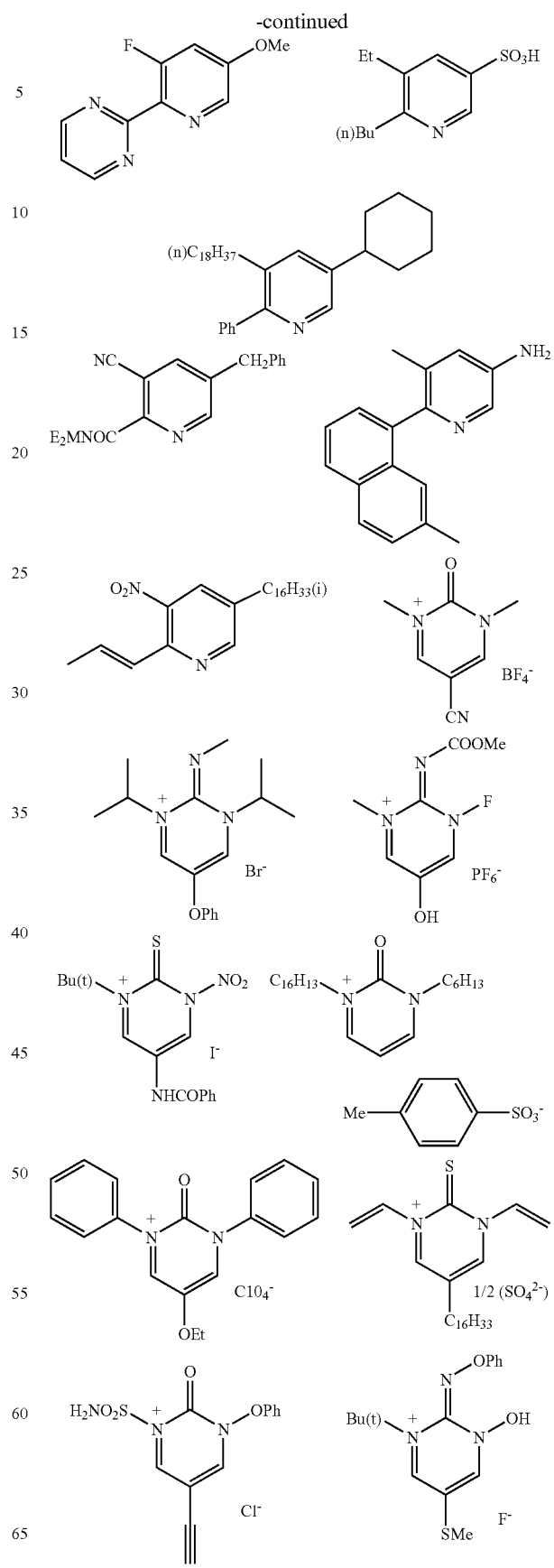

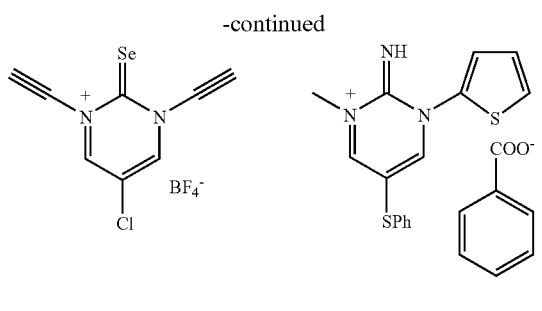
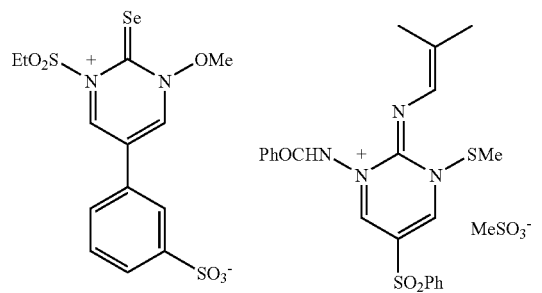
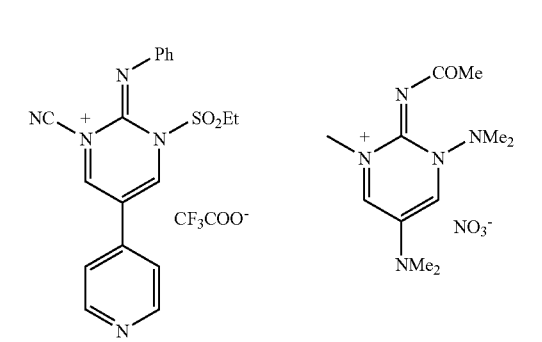
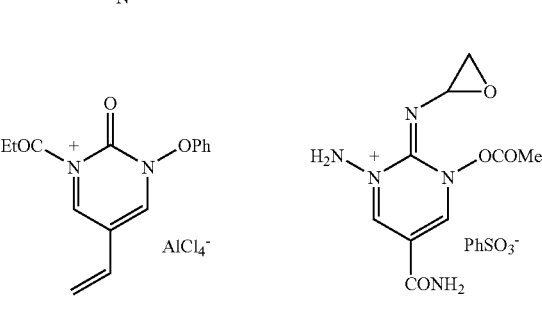
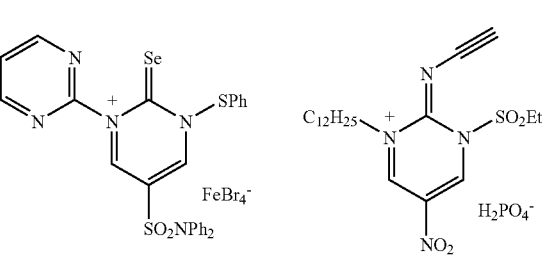
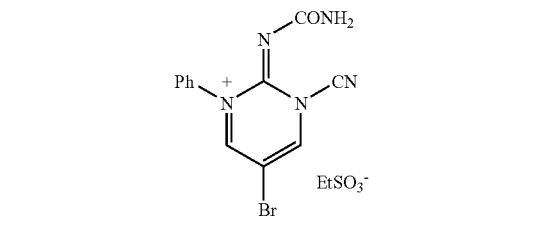
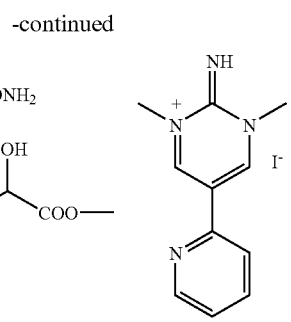
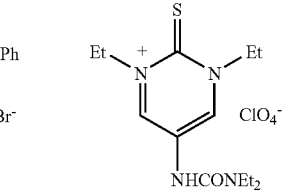
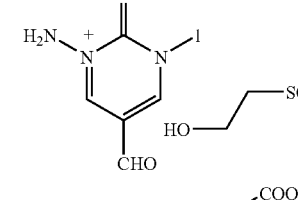
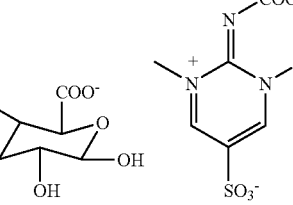
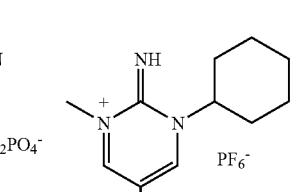
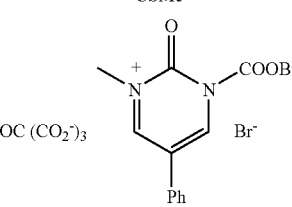
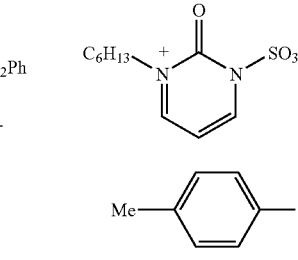

-continued
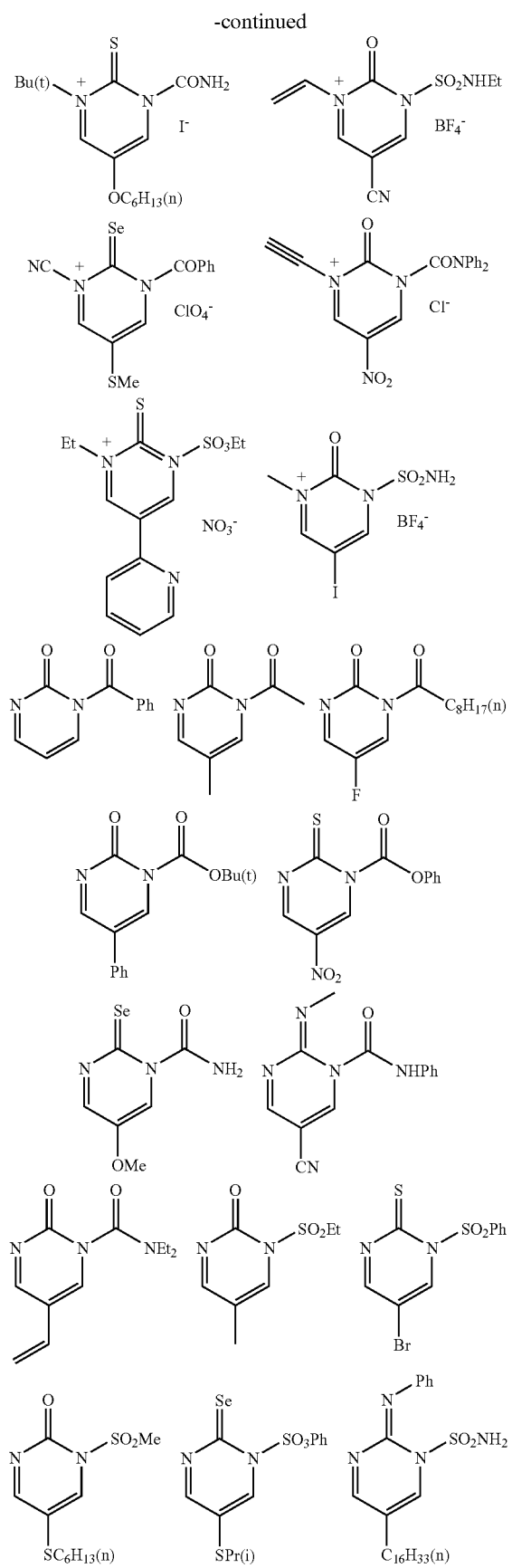
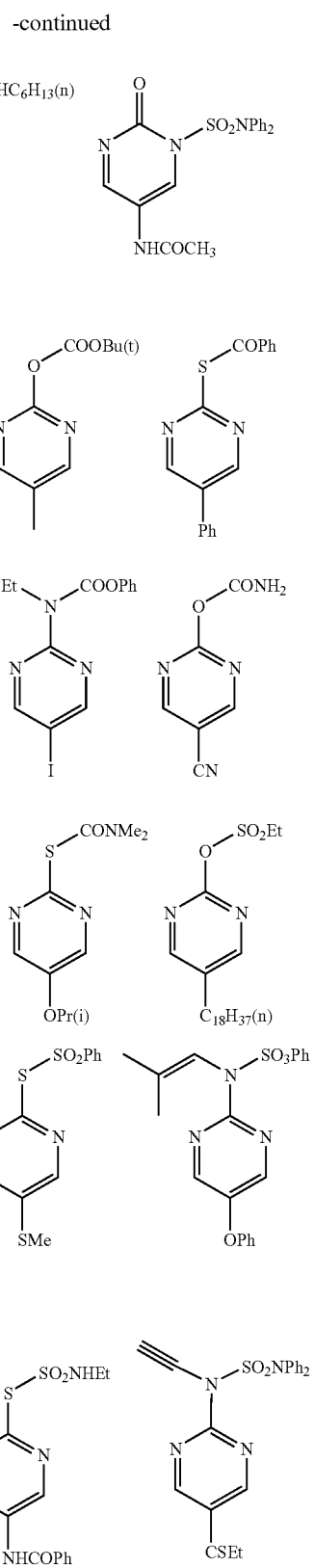
Next, the production methods of the invention are described in detail.

Firstly, the production method of a pyrimidinium derivative represented by the general formula (I) is described.

Various kinds of the bisacetal compound represented by the general formula (IV) are on the market and easily available. In addition, its synthesis method is broadly known, and it can be synthesized for example by reacting a vinyl ether compound with triethyl orthoformate by the method described in U.S. Pat. No. 2,556,312.

Synthesis method of the acrolein compound represented by the general formula (V) is broadly known, and it can be synthesized for example by subjecting an α-substituted carboxylic acid derivative to the Vilsmeier reaction and then hydrolyzing the product, as shown in the method described in Collect. Czech. Chem. Commun., p. 3051 (1961).

Various kinds of the urea compound represented by the general formula (IV) are also on the market and easily available.

Amount of the urea compound to be used in this reaction is from 0.1 to 10 mol, preferably from 0.5 to 5.0 mol, more preferably from 0.8 to 2.0 mol, based on 1 mol of the bisacetal compound or acrolein compound.

Reaction temperature of the urea compound with the bisacetal compound or acrolein compound is within the range of from −80 to 200° C., preferably from 20 to 18° C., more preferably from 30 to 150° C. Their reaction is completed generally within 24 hours, and disappearance of the materials is confirmed after 10 minutes to 2 hours in most cases.

Regarding the condensation reaction of the urea compound with the bisacetal compound or acrolein compound according to the invention, the reaction progresses by the substrates alone, but any one of a) an acid, b) a base and c) a base and an acid catalyst may be added in response to the condition.

When an acid is used in this reaction, examples of the acid to be used include acetic acid, methanesulfonic acid, trifluoroacetic acid, nitrophenol, chlorothiophenol and the like organic acids; and hydrochloric acid, sulfuric acid, nitric acid, titanium tetrachloride, aluminum trichloride and the like inorganic acids. Among them, acetic acid and hydrochloric acid are inexpensive and give good result. Amount of the acid to be used is within the range of from 0.01 to 6.0 mol, preferably from 0.3 to 3.5 mol, more preferably from 0.9 to 1.5 mol, based on 1 mol of the urea compound.

When a base is used in this reaction, examples of the base to be used include potassium tert-butoxide, sodium tert-butoxide, sodium ethoxide and the like metal alkoxides; n-butyl lithium, methylmagnesium chloride and the like organic metals; sodium borohydride, metallic sodium, lithium hydroxide, calcium oxide and the like inorganic bases; and triethylamine, diisopropylamine, 1,8-diazabicyclo[5,4,0]undeca-7-ene, pyridine, potassium acetate, tetrabutylammonium hydroxide, methylaniline and the like organic bases. Preferred among them are potassium tert-butoxide, sodium tert-butoxide and sodium hydride, and more preferred is potassium tert-butoxide. Amount of the aforementioned base is within the range of from 0.1 to 10 mol, preferably from 0.8 to 2.0 mol, more preferably from 0.9 to 1.2 mol, based on 1 mol of the urea compound.

When a base and an acid catalyst are used in this reaction, examples of the base to be used include anhydrous sodium carbonate, lithium hydroxide, potassium phosphate, calcium oxide and the like inorganic bases; and triethylamine, pyridine, potassium acetate, tetrabutylammonium hydroxide, methylaniline and the like organic bases. Among them, triethylamine, pyridine and anhydrous sodium carbonate are desirable because these are inexpensive and give good result. Amount of the base to be used in this case is within the range of from 0.1 to 10 mol, preferably from 0.8 to 8.0 mol, more preferably from 2.1 to 4.0 mol, based on 1 mol of the urea compound.

On the other hand, examples of the acid catalyst to be used jointly therewith include acetic anhydride, benzoic anhydride and the like acid anhydrides; N,N'-carbonyldiimidazole, dicyclohexylcarbodiimide and the like acid amides; acetyl chloride, benzoyl chloride, chlorosulfonic acid, N,N'-dimethylsulfamoyl chloride and the like acidhalides; polyphosphoric acid, titanium tetrachloride, aluminum trichloride, titanium trifurate, hafnium chloride and the like inorganic acid; and acetic acid, propionic acid and the like organic acids. Preferred are acetic anhydride, N,N'-carbonyldiimidazole, chlorosulfonic acid and acetyl chloride, and more preferred are chlorosulfonic acid and acetyl chloride. Amount of these acid catalysts to be used is within the range of from 0.01 to 6.0 mol, preferably from 0.1 to 3.5 mol, more preferably from 0.3 to 2.5 mol, based on 1 mol of the urea compound.

After completion of the reaction, the pyrimidinium derivative of interest may be separated and purified or used as such in the next step by a one-pot process. In this connection, the term "one-pot process" as used herein means a method in which a synthesized material is used as such in the subsequent step without separating it. When it is separated, the pyrimidinium derivative is crystallized by cooling the reaction solution, but extraction using ethyl acetate, toluene or the like organic solvent and water, recrystallization using an alcohol, hexane, toluene or the like, adsorption using activated carbon or the like, distillation under a reduced pressure and the like may be carried out as occasion demands. It is possible to obtain the product of interest with a high purity, by carrying out its purification using these methods alone or as a combination of two or more.

Next, the production method of a pyridine derivative is described.

According to the invention, the pyrimidinium derivative may be subjected to condensation reaction with an acetyl compound and then subjected to cyclization reaction in the presence of ammonia or an ammonium salt, or the pyrimidinium derivative, an acetyl compound and ammonia or an ammonium salt may be simultaneously added to carry out the reaction.

Various kinds of the acetyl compound to be used in the invention represented by the general formula (II) are on the market, or can be easily synthesized by introducing acyl group into the backbone of interest by a conventionally known method such as Friedel-Craft's reaction.

In addition to the aforementioned synthesis method, when R2 or R3 is carbonyl group or sulfonyl group, the pyrimidinium derivative represented by the general formula (I) to be used in the invention may be used by forming the pyrimidinium derivative in the system through the reaction of a pyrimidone compound represented by the general formula (VIII) with acetic anhydride or the like carbonization agent or methanesulfonyl chloride or the like sulfonization agent in the reaction solution.

Amount of the pyrimidinium derivative to be used is from 0.5 to 6.0 mol, preferably from 0.8 to 4.0 mol, more preferably from 0.9 to 2.5 mol, based on 1 mol of the acetyl compound.

On the other hand, according to the invention, the reaction progresses in the same manner when the pyrimidone compound represented by the general formula (VIII) or a pyrimidine compound represented by the general formula (IX) is subjected to condensation reaction with an acetyl compound.

The pyrimidone compound (VIII) and pyrimidine compound (IX) of the invention can be synthesized from urea, thiourea or a guanidine derivative and a malonaldehyde derivative by a conventionally known method such as the method described in "Helvetica Chimica Acta, 305 (1927)", "J. Am. Chem. Soc., 91 (1912)" or the like. Also, they may be synthesized from precursors in which R12 in the general formula (VIII) and general formula (IX) is hydrogen, by reacting with acetic anhydride or the like carbonization agent or methanesulfonyl chloride or the like sulfonization agent in the reaction system.

Also, according to this reaction, it is possible to synthesize the pyrimidone compound and pyrimidine compound by these conventionally known methods, and then use them in the subsequent reaction with an acetyl compound without separating them.

In addition, when a pyrimidone compound or pyrimidine compound is used in this step, it may be directly used in the reaction or used by forming the pyrimidinium derivative in the system through the reaction with acetic anhydride or the like carbonization agent or methanesulfonyl chloride or the like sulfonization agent in the reaction system.

According to the invention, the pyrimidone compound or pyrimidine compound may be subjected to condensation reaction with an acetyl compound and then subjected to cyclization reaction in the presence of ammonia or an ammonium salt, or the pyrimidone compound or pyrimidine compound, an acetyl compound and ammonia or an ammonium salt may be simultaneously added to carry out the reaction.

Amount of the pyrimidone compound or pyrimidine compound to be used is from 0.5 to 6.0 mol, preferably from 0.8 to 4.0 mol, more preferably from 0.9 to 2.5 mol, based on 1 mol of the acetyl compound.

When any one of the pyrimidinium derivative, pyrimidone compound and pyrimidine compound is subjected to condensation reaction with the acetyl compound, and then cyclization reaction is carried out in the presence of ammonia or an ammonium salt, the reaction temperature in carrying out the condensation reaction is within the range of from −80 to 200° C., preferably from −80 to 120° C., more preferably from −10 to 100° C. The condensation reaction is completed generally within 24 hours, and disappearance of the materials is confirmed after 10 minutes to 12 hours in most cases.

The condensation reaction of any one of the pyrimidinium derivative, pyrimidone compound and pyrimidine compound with the acetyl compound progresses by the substrates alone, but anyone of a) an acid, b) a base and c) a base and an acid catalyst may be added in response to the condition.

When a base is added in this reaction, examples of the base to be used include potassium tert-butoxide, sodiumethoxide and the like metal alkoxides; n-butyl lithium, methylmagnesium chloride and the like organic metals; sodium borohydride, metallic sodium, potassium hydroxide, calcium oxide and the like inorganic bases; and triethylamine, diisopropylamine, pyridine, potassium acetate, tetrabutylammonium hydroxide, methylaniline, 1,8-diazabicyclo[5,4,0]undeca-7-ene and the like organic bases. Preferred among them are potassium tert-butoxide, sodium tert-butoxide and sodium hydride, and more preferred is potassium tert-butoxide. Amount of the aforementioned base is within the range of from 0.1 to 10 mol, preferably from 0.8 to 2.0 mol, more preferably from 0.9 to 1.2 mol, based on 1 mol of the acetyl compound.

When an acid is added in this reaction, examples of the acid to be used include acetic acid, propionic acid, methanesulfonic acid, trifluoroacetic acid, nitrophenol, chlorothiophenol and the like organic acids; and hydrochloric acid, sulfuric acid, phosphoric acid, , aluminum trichloride, titanium trifurate, hafnium chloride and the like inorganic acids. Among them, acetic acid and propionic acid are desirable because they are inexpensive and give good result. Amount of the acid to be used is within the range of from 0.01 to 6.0 mol, preferably from 0.3 to 3.5 mol, more preferably from 2.0 to 3.0 mol, based on 1 mol of the acetyl compound.

When a base and an acid catalyst are added in this reaction, examples of the base to be used include anhydrous sodium carbonate, lithium hydroxide, potassium phosphate, calcium oxide and the like inorganic bases; and triethylamine, pyridine, potassium acetate, tetrabutylammonium hydroxide, methylaniline and the like organic bases. Among them, triethylamine, pyridine and anhydrous sodium carbonate are desirable because these are inexpensive and give good result. Amount of the aforementioned base to be used is within the range of from 0.1 to 10 mol, preferably from 0.8 to 8.0 mol, more preferably from 2.1 to 4.0 mol, based on 1 mol of the acetyl compound.

On the other hand, examples of the acid catalyst to be used jointly with the base include acetic anhydride, benzoic anhydride and the like acid anhydrides; N,N'-carbonyldiimidazole, dicyclohexylcarbodiimide and the like acid amides; acetyl chloride, benzoyl chloride, chlorosulfonic acid, N,N'-dimethylsulfamoyl chloride and the like acid halides; polyphosphoric acid, titanium tetrachloride, aluminum trichloride, titanium trifurate, hafnium chloride and the like inorganic acid; and acetic acid, propionic acid and the like organic acids. Preferred are acetic anhydride, N,N'-carbonyldiimidazole, chlorosulfonic acid and acetyl chloride, and more preferred are chlorosulfonic acid and acetyl chloride. Amount of these acid catalysts to be used is within the range of from 0.01 to 6.0 mol, preferably from 0.3 to 3.5 mol, more preferably from 0.5 to 2.0 mol, based on 1 mol of the acetyl compound.

When a cyclization reaction is carried out in the presence of ammonia or an ammonium salt after the aforementioned condensation reaction, or when any one of the pyrimidinium derivative, pyrimidone compound and pyrimidine compound is added simultaneously with the acetyl compound and ammonia or an ammonium salt, the ammonia or ammonium salt to be used in either case can be used in any form. Ammonia gas, aqueous ammonia, ammonium chloride, ammonium acetate, ammonium formate, acetamide, sodium amide and the like are generally used. Preferred among them are ammonium chloride, ammonium acetate and ammonium formate, and most preferred is ammonium acetate. Their amount to be used is within the range of from 1 to 30 mol, preferably from 2 to 15 mol, more preferably from 3 to 8 mol, based on 1 mol of the acetyl compound. In addition, two or more of different ammonia forms can be mixed and used, and the mixing ratio in using as a mixture can be optionally set.

In the production methods of the invention, a catalyst is not particularly necessary at the time of carrying out the cyclization reaction or when materials are simultaneously added, but it is preferable to use an acid catalyst as occasion demands, because the reaction is completed in a lot shorter period of time. Though any substance can be used as the acid catalyst, sulfuric acid, hydrochloric acid and the like inorganic acids, p-toluenesulfonic acid, formic acid, acetic acid, propionic acid and the like organic acids, Amberlite, Amberlist and the like strongly acidic ion exchange resins and the like are used, of which formic acid, acetic acid and propionic acid are desirable because of their ability to keep the reaction system weakly acidic, and acetic acid is more desirable. Amount of the acid catalyst to be used is within the range of from 0.001 to 3.0 mol, preferably from 0.005 to 1.0 mol, more preferably from 0.01 to 0.5 mol, based on 1 mol of the acetyl compound.

According to the invention, the temperature at the time of carrying out the cyclization reaction or when materials are simultaneously added is within the range of from −80 to 200° C., preferably from 0 to 150° C., more preferably from 60 to 120° C. These reactions are completed generally within 24 hours, and disappearance of the materials is confirmed after 10 minutes to 12 hours in most cases.

Next, the method in which anyone of the bisacetal compound, acrolein compound and malonaldehyde compound is reacted with the urea compound and acetyl compound simultaneously is described.

In this reaction it is not necessary to carryout successive reaction, and the pyridine derivative of interest can be obtained even when all of the materials are charged and the reaction is simultaneously carried out.

When the reaction is simultaneously carried out, the urea compound may be used in an equimolar amount based on the bisacetal compound, acrolein compound or malonaldehyde compound, but the reaction sufficiently progresses with a catalytically effective amount. The reason for this is that the pyrimidinium derivative is generated in this case and further undergoes the reaction to form the pyridine derivative, and the urea compound is regenerated at the same time and again incorporated into the reaction to act in a catalytic manner. The reaction scheme is described below.

from 0.1 to 10 mol, preferably from 0.5 to 5.0 mol, more preferably from 0.8 to 2.0 mol, based on 1 mol of the acetyl compound.

Amount of ammonia or an ammonium salt to be used is within the range of from 1 to 30 mol, preferably from 2 to 15 mol, more preferably from 3 to 10 mol, based on 1 mol of the acetyl compound.

The reaction temperature is within the range of from −80 to 200° C., preferably from 0 to 150° C., more preferably from 60 to 130° C. These reactions are completed generally within 24 hours, and disappearance of the materials is confirmed after 10 minutes to 12 hours in most cases.

This reaction progresses by the substrates alone, but anyone of a) an acid, b) a base and c) a base and an acid catalyst may be added in response to the condition.

When an acid is added in this reaction, examples of the acid to be used include acetic acid, propionic acid, methanesulfonic acid, trifluoroacetic acid, nitrophenol, chlorothiophenol and the like organic acids; and hydrochloric acid, sulfuric acid, phosphoric acid, , aluminum trichloride, titanium trifurate, hafnium chloride and the like inorganic acids. Among them, acetic acid and propionic acid are desirable because they are inexpensive and give good result. Amount of the acid to be used is within the range of from 0.01

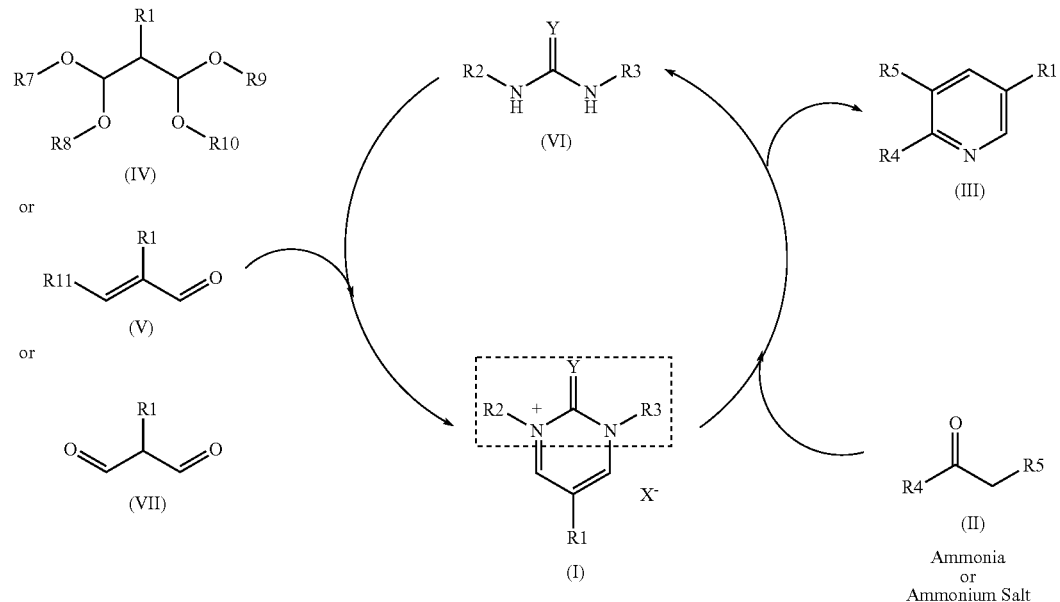

Various kinds of the malonaldehyde compound represented by the general formula (VII) to be used in this reaction are on the market and can be easily obtained.

Amount of the urea compound to be used in this reaction is within the range of from 0.001 to 10 mol, preferably from 0.01 to 5.0 mol, more preferably from 0.08 to 3.0 mol, based on 1 mol of the acetyl compound. When a catalytically effective amount of the urea compound is used, it is within the range of from 0.001 to 1 mol, preferably from 0.005 to 0.5 mol, more preferably from 0.05 to 0.3 mol, based on 1 mol of the acetyl compound.

Amount of the bisacetal compound, acrolein compound or malonaldehyde compound to be used is within the range of to 6.0 mol, preferably from 0.3 to 3.5 mol, more preferably from 2.0 to 3.0 mol, based on 1 mol of the acetyl compound.

When a base is added in this reaction, examples of the base to be used include potassium tert-butoxide, sodium ethoxide and the like metal alkoxides; n-butyl lithium, methylmagnesium chloride and the like organic metals; sodium borohydride, metallic sodium, potassium hydroxide, calcium oxide and the like inorganic bases; and triethylamine, diisopropylamine, pyridine, potassium acetate, tetrabutylammonium hydroxide, methylaniline, 1,8-diazabicyclo[5,4,0]undeca-7-ene and the like organic bases. Preferred among them are potassium tert-butoxide, sodium tert-butoxide and sodium hydride, and more preferred is potassium tert-butoxide. Amount of the aforementioned base is within the range of from 0.1 to 10 mol, preferably from 0.8 to 2.0 mol, more preferably from 0.9 to 1.2 mol, based on 1 mol of the acetyl compound.

When a base and an acid catalyst are added in this reaction, examples of the base to be used include anhydrous sodium carbonate, lithium hydroxide, potassium phosphate, calcium oxide and the like inorganic bases; and triethylamine, pyridine, potassium acetate, tetrabutylammonium hydroxide, methylaniline and the like organic bases. Among them, triethylamine, pyridine and anhydrous sodium carbonate are desirable because these are inexpensive and give good result. Amount of the aforementioned base to be used is within the range of from 0.1 to 10 mol, preferably from 0.1 to 3.5 mol, more preferably from 0.3 to 2.0 mol, based on 1 mol of the acetyl compound.

On the other hand, examples of the acid catalyst to be used jointly with the base include acetic anhydride, benzoic anhydride and the like acid anhydrides; N,N'-carbonyldiimidazole, dicyclohexylcarbodiimide and the like acid amides; acetyl chloride, benzoyl chloride, chlorosulfonic acid, N,N'-dimethylsulfamoyl chloride and the like acid halides; polyphosphoric acid, , aluminum trichloride, titanium trifurate, hafnium chloride and the like inorganic acid; and acetic acid, propionic acid and the like organic acids. Preferred are acetic anhydride, N,N'-carbonyldiimidazole, chlorosulfonic acid and acetyl chloride, and more preferred are chlorosulfonic acid and acetyl chloride. Amount of these acid catalysts to be used is within the range of from 0.01 to 6.0 mol, preferably from 0.3 to 3.5 mol, more preferably from 0.5 to 2.0 mol, based on 1 mol of the acetyl compound.

According to the invention, it is not necessary to use a reaction solvent throughout the all steps, but as occasion demands, any one of organic solvents or inorganic solvents can be used regardless of polar or non-polar, such as benzene, toluene, xylene, chlorobenzene, dichlorobenzene and the like aromatic solvents; pyridine, acetonitrile, N,N-dimethylformamide, N,N-dimethylacetamide, N-methylpyrrolidone and the like polar solvents; methyl acetate, ethyl acetate, butyl acetate and the like ester solvents; diethyl ether, diisopropyl ether, dibutyl ether, methyl-t-butyl ether, tetrahydrofuran (to be referred to as THF) and the like ether solvents; methanol, ethanol, isopropyl alcohol, butanol, tert-butanol and the like alcohol solvents; water and the like, of which preferred are methanol, ethanol, isopropyl alcohol and the like alcohol solvents, and more preferred is methanol. In addition, two or more solvents can be mixed and used, and the mixing ratio in using as a mixture can be optionally set. Amount of the aforementioned reaction solvent to be used is within the range of from 1 to 50 times in weight, preferably from 2 to 30 times in weight, more preferably from 3 to 5 times in weight, based on the acetyl compound.

As the method for carrying out purification of the pyridine derivative of interest after completion of the reaction, recrystallization using an alcohol, hexane, toluene or the like, column purification using silica gel, distillation under a reduced pressure and the like can be exemplified. By carrying out the purification using these methods alone or as a combination of two or more, it is possible to obtain the aimed compound with a high purity.

EXAMPLES

Next, the invention is described further illustratively based on examples, but the invention is not limited thereto. In this connection, evaluation of the purity was carried out by a high performance liquid chromatography (to be referred to as HPLC). The HPLC analysis conditions are as follows. Column: ODS-80TM, detection UV: 254 nm, flow rate: 1.0 ml/min., eluent: acetonitrile/water=50/50, and buffer: triethylamine and acetic acid each in 0.1%.

Example 1

Synthesis of 1,3-dimethyl-2,3-dihydro-2-oxopyrimidinium Chloride (I-1)

69.6 g (0.5 mol) of 3-piperidinoacrolein, 48.5 g (0.55 mol) of 1,3-dimethylurea and 130.2 g (1.25 mol) of 35% hydrochloric acid were dissolved in 400 ml of methanol and allowed to undergo the reaction at 50° C. for 2 hours. After completion of the reaction, this was cooled to 10° C., and the precipitated crystals were collected by filtration to obtain 90.1 g (yield 85%) of the title compound (purity 99.8%, melting point 174-175° C.).

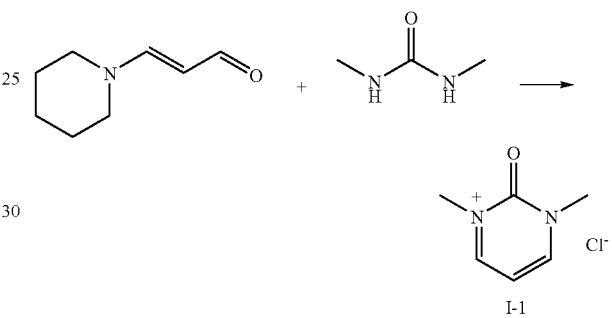

Example 2

Synthesis of 1,3-dimethyl-2,3-dihydro-2-oxopyrimidinium Sulfate (I-2)

82.1 g (0.5 mol) of 1,1,3,3-tetramethoxypropane and 39.7 g (0.45 mol) of 1,3-dimethylurea were dissolved in 400 ml of methanol, 49.0 g (0.5 mol) of concentrated sulfuric acid was added dropwise thereto at room temperature, and the mixture was allowed to undergo the reaction at 50° C. for 30 minutes. After completion of the reaction, this was cooled to room temperature, and the precipitated crystals were collected by filtration to obtain 59.7 g (yield 69%) of the title compound (purity 99.8%, melting point 203-205° C.).

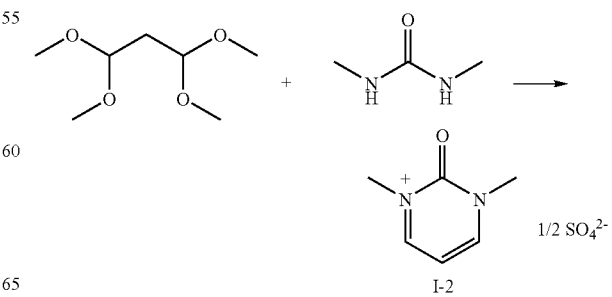

Example 3

Synthesis of 2,4'-bipyridine (III-1)

14.0 g (87 mmol) of 1,3-dimethyl-2,3-dihydro-2-oxopyrimidinium chloride obtained in Example 1 was dissolved in 25 ml of acetonitrile and mixed with 10 g (83 mmol) of 4-acetylpyridine, and 12.6 g (125 mmol) of triethylamine was added dropwise thereto at 45° C. or less. After 30 minutes of the reaction at 45° C., acetonitrile and triethylamine were evaporated under a reduced pressure, and 25 ml (416 mmol) of acetic acid and 39 g (454 mmol) of ammonium acetate were added to the residual liquid to carry out the reaction at 120° C. for 8 hours. After completion of the reaction, this was cooled to room temperature, neutralized with 217 g of 25% sodium hydroxide aqueous solution and then extracted three times with 200 ml of toluene. The organic layer was concentrated and then purified by distillation under a reduced pressure to obtain 10.3 g (yield 80%) of the title compound (purity 99.9%, melting point 56-57° C.).

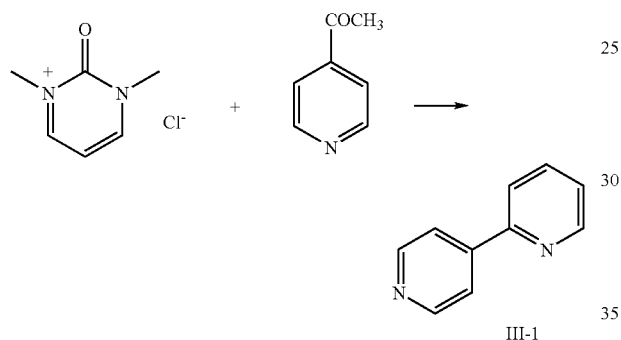

Example 4

Synthesis of 2,4'-bipyridine (III-1)

15.0 g (92 mmol) of 1,1,3,3-tetramethoxypropane and 20.5 g (119 mmol) of 1,3-di(n-butyl)urea were dissolved in 20 ml of 2-propanol, 13.0 g (125 mmol) of 35% hydrochloric acid was added thereto, and the mixture was refluxed for 1 hour. The reaction solution was cooled to room temperature, and 10.0 g (83 mmol) of 4-acetylpyridine and 7.1 g (89.8 mmol) of pyridine were added thereto. After 30 minutes of stirring at room temperature, 19 ml (416 mmol) of formic acid and 31.5 g (500 mmol) of ammonium formate were added to the reaction solution to carry out the reaction at 100° C. for 8 hours. After completion of the reaction, this was cooled to room temperature, neutralized with 200 g (1.2 mol) of 25% sodium hydroxide aqueous solution and then extracted three times with 200 ml of toluene. The organic layer was concentrated and then purified by distillation under a reduced pressure to obtain 9.9 g (yield 76.5%) of the title compound (purity 99.9%, melting point 55-57° C.).

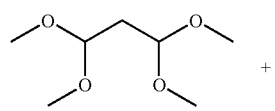

+

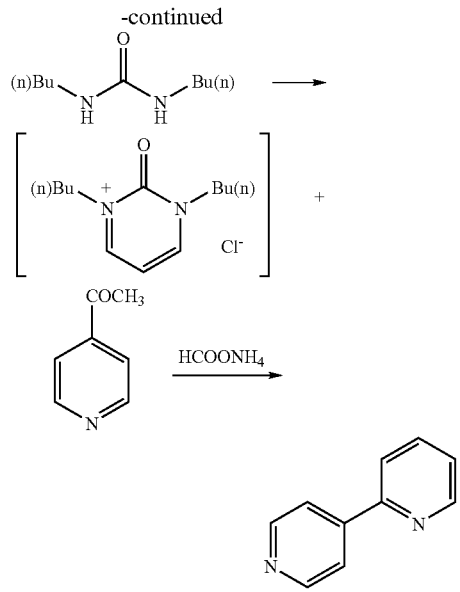

Example 5

Synthesis of 5-ethyl-2-cyclohexylpyridine (III-2)

8.71 g (87 mmol) of 2-ethylmalonaldehyde, 16.8 g (79 mmol) of 1,3-diphenylurea, 10.0 g (79 mmol) of methyl cyclohexyl ketone, 11.9 ml (198 mmol) of acetic acid and 39 g (500 mmol) of ammonium acetate were dissolved in 160 ml of 2-propanol, and 5.3 g (39.5 mmol) of chlorosulfonic acid was added dropwise thereto at room temperature. The reaction solution was allowed to undergo the reaction at 80° C. for 2 hours. After completion of the reaction, this was cooled to room temperature, neutralized with 200 g (1.2 mol) of 25% sodium hydroxide aqueous solution and then extracted three times with 200 ml of toluene. The organic layer was concentrated and then purified by distillation under a reduced pressure to obtain 10.8 g (yield 72%) of the title compound (purity 99.3%, melting point 79-81° C.).

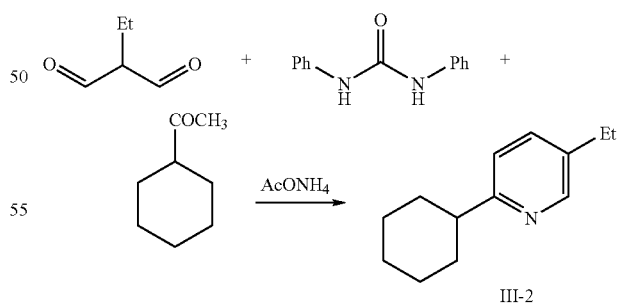

Example 6

Synthesis of 2,4'-bipyridine (III-1)

12.3 g (79 mmol) of 1,1,3,3-tetramethoxypropane, 0.12 g (0.8 mmol) of 1-methyl-3-phenylurea, 9.6 g (79 mmol) of 4-acetylpyridine, 30 ml (500 mmol) of acetic acid and 39 g (500 mmol) of ammonium acetate were dissolved in 160 ml of 2-propanol, and the reaction solution was allowed to undergo the reaction at 80° C. for 9 hours. After completion of the reaction, this was cooled to room temperature, neutralized with 200 g (1.2 mol) of 25% sodium hydroxide aqueous solution and then extracted three times with 200 ml of toluene. The organic layer was concentrated and then purified by distillation under a reduced pressure to obtain 7.8 g (yield 63.2%) of the title compound (purity 99.2%, melting point 55-57° C.).

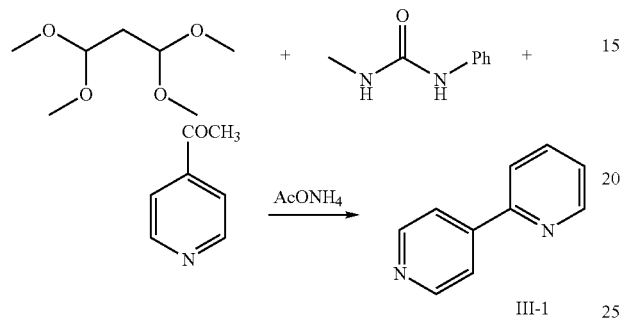

Example 7

Synthesis of 2-cyano-3-methylpyridine (III-3)

A 11.53 g (120 mmol) of 2-pyrimidone and 12.14 g (120 mmol) of triethylamine were dissolved in 50 ml of ethanol, and 11.23 g (110 mmol) of acetic anhydride was added dropwise thereto at 70° C. spending 1 hour. The reaction solution was cooled to room temperature and mixed with 8.31 g (100 mmol) of 2-oxobutyronitrile and 30.43 g (400 mmol) of ammonium acetate, and the resulting reaction solution was allowed to undergo the reaction at 80° C. for 4 hours. After completion of the reaction, this was cooled to room temperature, neutralized with 100 g (600 mmol) of 25% sodium hydroxide aqueous solution and then extracted twice with 40 ml of toluene. By concentrating the organic layer, 7.92 g (yield 67.1%) of the title compound was obtained (purity 99.1%, melting point 85-86° C.).

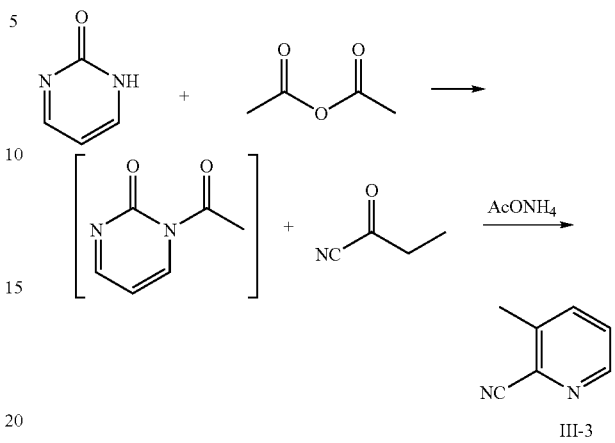

Examples 8 and 9

The following compounds were synthesized under the same conditions of Example 6, except that the acetyl compound, bisacetal compound and urea compound as the materials were changed to the compounds shown in Table 1.

Examples 10 and 11

The following compounds were synthesized under the same conditions of Example 5, except that the acetyl compound, malonaldehyde compound and urea compound as the materials were changed to the compounds shown in Table 1.

Examples 12 and 13

The following compounds were synthesized under the same conditions of Example 6, except that the material bisacetal compound was changed to the acrolein compound shown in Table 1, and the acetyl compound and urea compound were also changed to the respective compounds shown in Table 1. The results of Examples 8 to 13 are shown in Table 1.

TABLE 1

| Example Compound No. | Material Acetyl Compound | Malonaldehyde or Bisacetal Acrolein | Material Urea Compound | Yield (%) | Purity (%) | Melting Point (° C.) |
|---|---|---|---|---|---|---|
| 8 (III-4) | COCH₃–Ph | EtO–CH(Bu(n))–CH(OEt)₂, OEt | Ph-NH-C(O)-NH-CN | 65.2 | 99.1 | 34–35 |
| 9 (III-5) | COCH₃–Ph | (n)BuO–C(OBu(n))(OMe)–CH(OBu(n))₂ | Ph-NH-C(O)-NH-CN | 67.0 | 99.3 | 55–56 |

TABLE 1-continued

| Example Compound No. | Material Acetyl Compound | Malonaldehyde or Bisacetal Acrolein | Material Urea Compound | Yield (%) | Purity (%) | Melting Point (°C.) |
|---|---|---|---|---|---|---|
| 10 (III-6) | 4-methylphenyl-COCH₃ | OHC-CH(CF₃)-CHO | MeNH-C(=S)-NHMe | 75.9 | 99.0 | 129–130 |
| 11 (III-7) | NC-CH₂-CHO | 4-(C₇H₁₅)-cyclohexyl-CH(CHO)₂ | PhNH-C(=N-OH)-NH-Pr(i) | 48.5 | 99.0 | 50–51 (Crystal-Nematic) 60–61 (Nematic-Liquid) |
| 12 (III-8) | cyclopentanone | MeO-CH=C(NO₂)-CHO | PhNH-C(=Se)-NHPh | 82.0 | 99.6 | 94–95 |
| 13 (III-9) | F₃C-CO-CH₂-CH(COOH)- | Ph₂N-CH=C(Br)-CHO | (t)Bu-NH-C(=O)-NH-Bu(t) | 72.1 | 99.3 | 152–153 |

III-4: 5-(n-Bu)-2-phenylpyridine

III-5: 5-OMe-2-phenylpyridine

III-6: 5-CF₃-2-(4-methylphenyl)pyridine

TABLE 1-continued

| Example Compound No. | Material Acetyl Compound | Malonaldehyde or Bisacetal Acrolein | Material Urea Compound | Yield (%) | Purity (%) | Melting Point (° C.) |
|---|---|---|---|---|---|---|
| III-7 | | | | | | |
| III-8 | | | | | | |
| III-9 | | | | | | |

Example 14

Synthesis of ethyl 5-cyanonicotinate (III-10)

31.4 g (120 mmol) of 2-oxo-1-(phenylsulfonyl)-1,2-dihydropyrimidine-5-carbonitrile and 10.2 g (100 mmol) of ethyl oxo-acetate were dissolved in 250 ml of ethanol, and allowed to undergo the reaction at 70° C. for 2 hours. 30.4 g (400 mmol) of ammonium acetate was added to the reaction solution to carry out the reaction at 90° C. for 4 hours. After completion of the reaction, this was cooled to room temperature, neutralized with 100 g (600 mmol) of 25% sodium hydroxide aqueous solution and then extracted twice with 40 ml of toluene. By concentrating the organic layer, 12.1 g (yield 68.7%) of the title compound was obtained (purity 98.2%, melting point 58-59° C.)

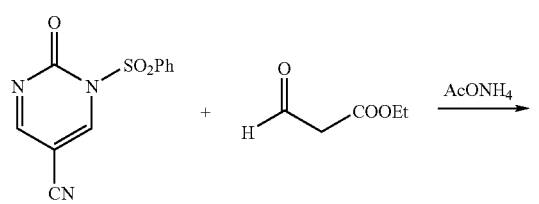

Example 15

Synthesis of ethyl 5-cyanonicotinate (III-10)

The procedure of Example 14 was repeated under the same conditions, except that the 2-oxo-1-(phenylsulfonyl)-1,2-dihydropyrimidine-5-carbonitrile of Example 14 was changed to tert-butyl(5-cyanopyrimidin-2-yl)methylcarbamate, thereby obtaining 10.6 g (yield 60.2%) of the title compound (purity 98.0%, melting point 58-59° C.)

Comparative Example 1

Synthesis of 2,4'-bipyridine (III-1)

14.2 g (87 mmol) of 1,1,3,3-tetramethoxypropane, 10 g (83 mmol) of 4-acetylpyridine, 30 ml (500 mmol) of acetic acid and 39 g (500 mmol) of ammonium acetate were dissolved in 160 ml of 2-propanol, and the reaction solution was allowed to undergo the reaction at 80° C. for 9 hours. After completion of the reaction, this was cooled to room temperature, neutralized with 200 g (1.2 mol) of 25% sodium hydroxide aqueous solution and then extracted three times with 200 ml of toluene. The organic layer was concentrated and then purified by distillation under a reduced pressure to obtain 3.2 g (yield 27.6%) of the title compound (purity 98.2%).

Results of Examples 3 and 6 and Comparative Example 1 are compared in the following Table 2.

TABLE 2

|  | Yield (%) | Purity (%) |
|---|---|---|
| Example 3 | 80.0 | 99.9 |
| Example 6 | 63.2 | 99.2 |
| Comparative Example 1 | 27.6 | 98.2 |

Yield and quality of Example 3 were superior to those of other Examples. Though the process was simplified in Example 6, it was able to obtain the title compound with sufficient yield and quality. Since the yield was high in comparison with Comparative Example 1, superiority of the present method is evident. In addition, since the starting materials used in this method are on the market in large amounts and inexpensive, it is evident that the synthesis can be carried out at a lower cost than other methods.

According to the invention, a pyridine derivative, an important intermediate in the field of medicines, agricultural chemicals, catalytic ligands, combinatorial chemistry, organic electroluminescence elements, charge transport materials, electron transport materials, electron transport materials, electrophotographic photo-sensitive materials, dyes, liquid crystals and the like, can be produced on an industrial scale without using an expensive catalyst and a special device. Particularly, according to the invention, a regiospecific pyridine derivative can be produced at a high purity, a high yield and a low cost without causing a pollution problem.

The entire disclosure of each and every foreign patent application from which the benefit of foreign priority has been claimed in the present application is incorporated herein by reference, as if fully set forth.

What is claimed is:

1. A method for producing a pyridine derivative represented by formula (III) below, the method comprising reacting a pyrimidinium derivative represented by formula (I) below, an acetyl compound represented by formula (II) below and an ammonia or an ammonium salt:

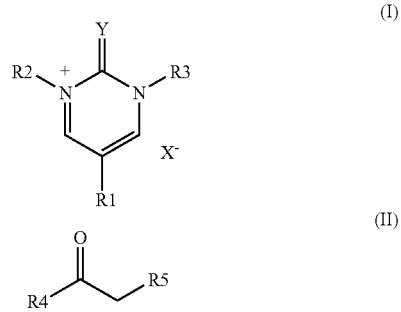

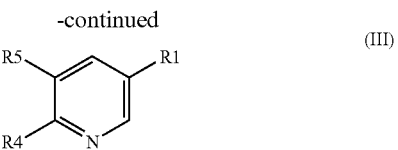

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, cyano group, halogen atom or hetero ring;

R2 represents alkyl group, alkenyl group, alkynyl group, aryl group, carbonyl group, sulfonyl group, carbamoyl group, sulfamoyl group, amino group, ureido group, carbonylamino group, sulfonylamino group, cyano group or hetero ring;

R3 represents alkyl group, alkenyl group, alkynyl group, aryl group, hydroxyl group, alkoxy group, aryloxy group, carbonyloxy group, alkylthio group, arylthio group, carbonyl group, oxycarbonyl group, sulfonyl group, carbamoyl group, sulfamoyl group, amino group, ureido group, carbonylamino group, sulfonylamino group, nitro group, cyano group, hetero ring or halogen atom;

R4 represents hydrogen atom, alkyl group, alkenyl group, alkynyl group, aryl group, amino group, formyl group, carboxyl group, carbonyl group, oxycarbonyl group, sulfo group, sulfonyl group, carbamoyl group, sulfamoyl group, cyano group or hetero ring;

R5 represents hydrogen atom, alkyl group, alkenyl group, alkynyl group, aryl group, hydroxyl group, alkoxy group, aryloxy group, carbonyloxy group, formyl group, carboxyl group, carbonyl group, oxycarbonyl group, sulfonyl group, alkylthio group, arylthio group, carbamoyl group, sulfamoyl group, nitro group, cyano group, hetero ring or halogen atom, wherein R4 and R5 may be bonded to form a ring consisting of at least one non-metallic atom, the ring including the carbon atoms to which R4 and R5 are bonded;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring, wherein R6 may be bonded with R2 or R3 to form a hetero ring including the nitrogen atom to which R2 or R3 is bonded; and X⁻ represents an anion.

2. The method for producing the pyridine derivative according to claim 1, wherein an amount of the pyrimidinium derivative is from 0.5 to 6.0 mol based on 1 mol of the acetyl compound.

3. The method for producing the pyridine derivative according to claim 1, further comprising:

reacting at least one of a bisacetal compound represented by formula (IV) below and an acrolein compound represented by formula (V) below with a urea compound represented by formula (VI) below to produce the pyrimidinium derivative represented by formula (I); and reacting the pyrimidinium derivative with the acetyl compound represented by formula (II) in a one-pot process:

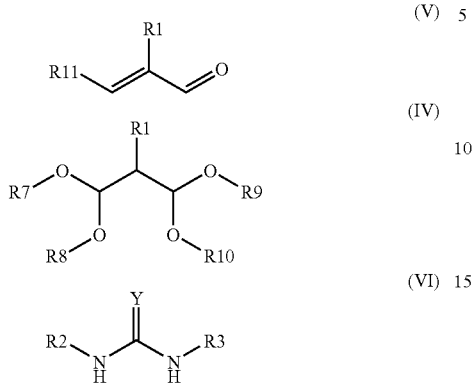

wherein R1 or R3 and Y are the same as defined in claim 1;
R7 to R10 each independently represents alkyl group, wherein two of R7 to R10 may be bonded to form a ring consisting of at least one non-metallic atom, the ring including the oxygen atoms to which said two of R7 to R10 are bonded; and
R11 represents alkoxy group, aryloxy group, di-substituted amino group or hetero ring.

4. A method for producing a pyridine derivative represented by formula (III) below, the method comprising a simultaneous reaction with at least one of a bisacetal compound represented by (IV) below, an acrolein compound represented by formula (V) below and a malonaldehyde compound formula (VII) below, with a urea compound represented by formula (VI) below and an acetyl compound represented by formula (II) below:

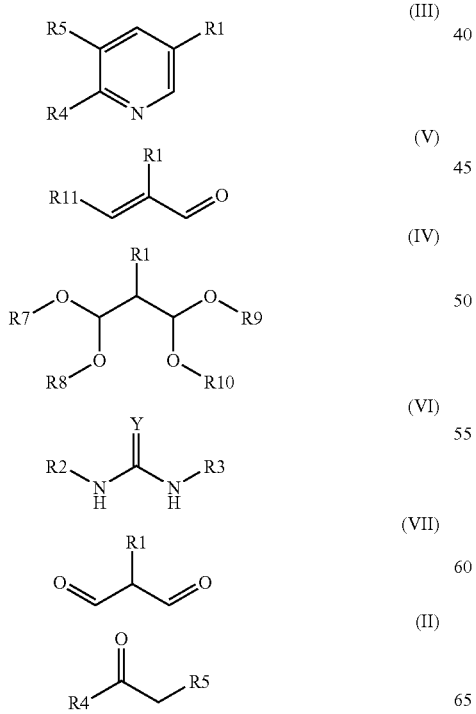

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, cyano group, halogen atom or hetero ring;

R2 represents alkyl group, alkenyl group, alkynyl group, aryl group, carbonyl group, sulfonyl group, carbamoyl group, sulfamoyl group, amino group, ureido group, carbonylamino group, sulfonylamino group, cyano group or hetero ring;

R3 represents alkyl group, alkenyl group, alkynyl group, aryl group, hydroxyl group, alkoxy group, aryloxy group, carbonyloxy group, alkylthio group, arylthio group, carbonyl group, oxycarbonyl group, sulfonyl group, carbamoyl group, sulfamoyl group, amino group, ureido group, carbonylamino group, sulfonylamino group, nitro group, cyano group, hetero ring or halogen atom;

R4 represents hydrogen atom, alkyl group, alkenyl group, alkynyl group, aryl group, amino group, formyl group, carboxyl group, carbonyl group, oxycarbonyl group, sulfo group, sulfonyl group, carbamoyl group, sulfamoyl group, cyano group or hetero ring;

R5 represents hydrogen atom, alkyl group, alkenyl group, alkynyl group, aryl group, hydroxyl group, alkoxy group, aryloxy group, carbonyloxy group, formyl group, carboxyl group, carbonyl group, oxycarbonyl group, sulfonyl group, alkylthio group, arylthio group, carbamoyl group, sulfamoyl group, nitro group, cyano group, hetero ring or halogen atom, wherein R4 and R5 may be bonded to form a ring consisting of at least one non-metallic atom, the ring including the carbon atoms to which R4 and R5 are bonded;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring , wherein R6 may be bonded with R2 or R3 to form a hetero ring including the nitrogen atom to which R2 or R3 is bonded;

R7 to R10 each independently represents alkyl group, wherein two of R7 to R10 may be bonded to form a ring consisting of at least one non-metallic atom, the ring including the oxygen atoms to which said two of R7 to R10 are bonded; and R11 represents alkoxy group, aryloxy group, di-substituted amino group or hetero ring.

5. The method for producing the pyridine derivative according to claim 4,
wherein an amount of the urea compound is from 0.001 to 10 mol based on 1 mol of the acetyl compound.

6. The method for producing the pyridine derivative according to claim 4,
wherein an amount of said at least one of the bisacetal compound, the acrolein compound and the malonaldehyde compound is from 0.1 to 10 mol based on 1 mol of the acetyl compound.

7. A method for producing a pyridine derivative represented by formula (III) below, the method comprising reacting at least one of a pyrimidone compound represented by formula (VIII) below and a pyrimidine compound represented by formula (IX) below, an acetyl compound represented by formula (II) below and an ammonia or an ammonium salt:

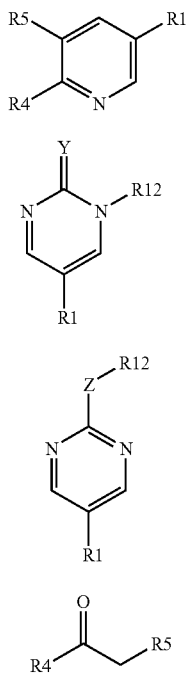

(III)

(VIII)

(IX)

(II)

wherein R1 represents hydrogen atom, alkyl group, alkenyl group, alkynyl group, aryl group, hydroxyl group, alkoxy group, aryloxy group, carbonyloxy group, alkylthio group, arylthio group, formyl group, carboxyl group, carbonyl group, thiocarbonyl group, sulfo group, sulfonyl group, carbamoyl group, sulfamoyl group, amino group, ureido group, carbonylamino group, sulfonylamino group, cyano group, halogen atom or hetero ring;

R4 represents hydrogen atom, alkyl group, alkenyl group, alkynyl group, aryl group, amino group, formyl group, carboxyl group, carbonyl group, oxycarbonyl group, sulfo group, sulfonyl group, carbamoyl group, sulfamoyl group, cyano group or hetero ring;

R5 represents hydrogen atom, alkyl group, alkenyl group, alkynyl group, aryl group, hydroxyl group, alkoxy group, aryloxy group, carbonyloxy group, formyl group, carboxyl group, carbonyl group, oxycarbonyl group, sulfonyl group, alkylthio group, arylthio group, carbamoyl group, sulfamoyl group, nitro group, cyano group, hetero ring or halogen atom, wherein R4 and R5 may be bonded to form a ring consisting of at least one non-metallic atoms, the ring including the carbon atoms to which R4 and R5 are bonded;

Y represents oxygen atom, sulfur atom, selenium atom or —N(R6);

R6 represents hydrogen atom, alkyl group, alkenyl group, alkynyl group, aryl group, hydroxyl group, carbonyl group, oxycarbonyl group, sulfonyl group, carbamoyl group, sulfamoyl group, amino group or hetero ring, wherein R6 may be bonded with R2 or R3 to form a hetero ring including the nitrogen atom to which R2 or R3 is bonded;

R12 represents carbonyl group, sulfonyl group, carbamoyl group or sulfamoyl group;

Z represents oxygen atom, sulfur atom, selenium atom or —N(R13); and

R13 represents alkyl group, alkenyl group, alkynyl group or aryl group.

8. The method for producing the pyridine derivative according to claim 7, wherein an amount of said at least one of the pyrimidone compound and the pyrimidine compound is from 0.5 to 6.0 mol based on 1 mol of the acetyl compound.

* * * * *